(12) United States Patent
Inoue

(10) Patent No.: US 8,776,603 B2
(45) Date of Patent: Jul. 15, 2014

(54) METHOD AND SYSTEM FOR NON-DESTRUCTIVE TESTING

(75) Inventor: Takumi Inoue, Fukuoka (JP)

(73) Assignee: Kyushu University, National University Corporation, Fukuoka-Shi (JP)

(*) Notice: Subject to any disclaimer, the term of this patent is extended or adjusted under 35 U.S.C. 154(b) by 315 days.

(21) Appl. No.: 13/387,872

(22) PCT Filed: Jul. 30, 2010

(86) PCT No.: PCT/JP2010/062905
§ 371 (c)(1),
(2), (4) Date: Apr. 12, 2012

(87) PCT Pub. No.: WO2011/013802
PCT Pub. Date: Feb. 3, 2011

(65) Prior Publication Data
US 2012/0186349 A1    Jul. 26, 2012

(30) Foreign Application Priority Data

Jul. 31, 2009  (JP) .................................. 2009-179510

(51) Int. Cl.
*G01N 29/11*  (2006.01)
(52) U.S. Cl.
USPC .............................................. 73/600; 73/602
(58) Field of Classification Search
USPC .................... 73/600, 579, 599, 602
See application file for complete search history.

(56) References Cited

U.S. PATENT DOCUMENTS

| | | | | |
|---|---|---|---|---|
| 4,445,379 A | * | 5/1984 | Yamaguchi et al. | 73/631 |
| 4,648,276 A | * | 3/1987 | Klepper et al. | 73/599 |
| 4,723,553 A | * | 2/1988 | Miwa et al. | 600/442 |
| 5,663,502 A | * | 9/1997 | Nagashima et al. | 73/599 |

FOREIGN PATENT DOCUMENTS

| | | |
|---|---|---|
| JP | 2001-021541 | 1/2001 |
| JP | 2004-340807 | 12/2004 |
| JP | 3705960 B2 | 10/2005 |

OTHER PUBLICATIONS

Inoue, et al. "Estimation of Time-Varying Vibration Parameters by the Segmental Use of the Harmonic Wavelet"; Transactions of the Japanese Society of Mechanical Engineers [C], vol. 74, No. 741, pp. 101-109, May 2008, nine pages.
Inoue, et al. "Estimation of Inner State by Detecting the Frequency Modulation in Supersonic Wave"; Dynamics and Design Conference 2009, CD-ROM, No. 09/23 (Aug. 5, 2009 in Sapporo), six pages.
Toda, et al. "The Most Practical Course: Introduction and Applications of Wavelet Transform"; published by SoftBank Creative (2005), one page.

\* cited by examiner

*Primary Examiner* — J M Saint Surin
(74) *Attorney, Agent, or Firm* — Rankin, Hill & Clark LLP

(57) ABSTRACT

Provided herein is a non-destructive testing method capable of diagnosing a condition of an object to be tested using a single-pulse ultrasonic wave signal. An attenuation waveform of the single-pulse ultrasonic wave signal received by a receiving section 3 is wavelet transformed by a wavelet transform section 6 to obtain an envelope line $A(t)$ and a phase $\phi(t)$ of the attenuation waveform. A temporal change computing section 7 approximates the attenuation waveform by an approximation equation available for computation, using the envelope line $A(t)$ and the phase $\phi(t)$ of the attenuation waveform inputted from the wavelet transform section 6, and obtains the temporal change of instantaneous frequency of the attenuation waveform. A diagnosing section 8 diagnoses a condition of the object to be tested, based on the temporal change of the instantaneous frequency computed by the temporal change computing section 7.

17 Claims, 11 Drawing Sheets

METHOD AND SYSTEM FOR NON-DESTRUCTIVE TESTING

TECHNICAL FIELD

The present invention relates to a method and a system for non-destructive testing using an ultrasonic wave pulse.

BACKGROUND ART

Japanese Patent No. 3705960 (Patent Document 1) shows conventional ultrasonic testing. In conventional ultrasonic testing methods for diagnosis of abnormality or abnormal conditions, an ultrasonic wave, which has been entered into an object to be tested and reflected on a discontinuous or discrete interface, namely an abnormal portion, is measured in terms of a pulse (see FIG. 1A).

Japanese Patent Application Publication No. 2004-340807 (JP 2004-340807A) (Patent Document 2) discloses an ultrasonic testing method for detecting minute abnormality such as defects due to insufficient weld by entering an ultrasonic wave into the surface of contact and evaluating waveform distortion of a transmitted wave with respect to the incident wave. In this disclosure, the waveform of the transmitted wave is frequency analyzed with respect to the incident wave to obtain the fundamental and harmonic waves; the ratio of amplitudes between the fundamental wave and the harmonic wave is calculated; and the presence of minute abnormality such as defects due to insufficient weld is determined based on the calculated ratio of amplitudes.

It is difficult by the conventional methods to detect obscure closed cracks as shown in FIG. 1B since the ultrasonic wave transmits such cracks. In contrast therewith, the harmonic and sub-harmonic components as well as fundamental component of the ultrasonic wave are conditionally observed by entering a series of ultrasonic wave pulse signals as shown in FIG. 2 and letting the signals transmit the obscure cracks or closed cracks as shown in FIG. 1B. The series of ultrasonic pulse signals as shown in FIG. 2 are, for example, continuous or successive pulse signals including ½ (half) sub-harmonic components. Phenomena called "acoustic nonlinearity" occur when such continuous-pulse ultrasonic wave signals are used. Some attempts have been made to detect cracks and exfoliations, which could not be found by ordinary methods, by observing such phenomena.

RELATED ART DOCUMENTS

Patent Documents

Patent Document 1: Japanese Patent No. 3705960 (JP3705960)

Patent Document 2: Japanese Patent Application Publication No. 2004-340807 (JP2004-340807A)

DISCLOSURE OF INVENTION

Technical Problem

There are some problems with the non-destructive testing utilizing the acoustic nonlinearity occurring when the continuous-pulse ultrasonic wave signals are used as describe below.

(1) Most of general ultrasonic testing apparatuses are designed to generate single-pulse ultrasonic waves. For this reason, a specially-designed apparatus is needed to generate continuous-pulse ultrasonic waves as shown in FIG. 2.

(2) Wave interference likely occurs if the continuous-pulse ultrasonic waves are entered into multi-layered members which are likely to cause reflected waves to be generated. As a result, proper analysis cannot be performed in some cases.

An object of the present invention is to provide a method and a system for non-destructive testing that enable diagnosis of a condition of an object to be tested, which could not be done by conventional methods using a single-pulse ultrasonic wave signal.

Solution to Problem

According to a non-destructive testing method of the present invention, single-pulse ultrasonic wave signal is used for testing an object to be tested. In this disclosure, the term "a single-pulse ultrasonic wave signal" is not limited to a simple pulse having one period, but covers pulses having frequencies and the number of periods which are employed in ordinary single-pulse ultrasonic wave generators available for general ultrasonic testing apparatuses. Though it depends on the properties of an object to be tested, a single-pulse ultrasonic wave signal preferably has a frequency of 1 MHz to 10 MHz and one or two periods if the pulse signal is used for testing an object made of rubber, concrete, metal, etc.

The single-pulse ultrasonic wave signal, which has been entered into the object to be tested, is received in a receiving section. Then, an instantaneous frequency of an attenuation waveform of the received single-pulse ultrasonic wave signal and temporal change or temporal transition of the instantaneous frequency are computed. The received single-pulse ultrasonic wave signal may be a transmitted wave which has transmitted the object to be tested or a reflected wave which has been reflected inside the object to be tested. Here, the instantaneous frequency of the attenuation waveform may be reworded with the rate of instantaneous phase change of the attenuation waveform. For the description of "instantaneous frequency", for example, you may refer to "The Most Recent Practical Course: Introduction and Application of Wavelet Transform" (page 40) written by Hiroshi Toda, Tadashi Akira, and Hiroaki Kawabata and published by Softbank Creative Corp.

In the non-destructive testing method of the present invention, the condition of an object to be tested is diagnosed based on the temporal change of the instantaneous frequency. According to the inventor's study, the frequency of the attenuation waveform of the single-pulse ultrasonic wave signal, which has transmitted obscure cracks, tends to decrease. It is possible to discover an abnormal condition by observing the temporal change of the instantaneous frequency of the attenuation waveform of the single-pulse ultrasonic wave signal. Such abnormal condition could not be found by conventional methods using a single-pulse ultrasonic wave signal. The method of the present invention uses a single-pulse ultrasonic wave signal. Therefore, the method of the present invention is hardly affected by interference of reflected waves and is capable of detecting even a small amount of frequency change. In addition, the method of the present invention is higher in accuracy than conventional methods of detecting harmonic and sub-harmonic components.

For example, the instantaneous frequency of an attenuation waveform is obtained at predetermined intervals. The condition of the object to be tested may be diagnosed by comparing a pattern shape of temporal change of the instantaneous frequency in respect of the object to be tested with a pattern shape of temporal change of an instantaneous frequency, which is used as a reference and has been obtained in advance by measuring the temporal change of the instantaneous frequency in respect of the object known to be in a normal condition. It is arbitrary to employ what specific steps of diagnosis based on the temporal change of the instantaneous frequency.

It is also arbitrary how to obtain the instantaneous frequency of the attenuation waveform. For example, the instantaneous frequency may be obtained as follows. An attenuation waveform u(t) of the received single-pulse ultrasonic wave signal is obtained using an approximation equation of u(t)=A(t)sin φ(t) where t stands for time, A(t) for an envelope line of the attenuation waveform and φ(t) for a phase at time t. Then, an instantaneous angular frequency at time t is obtained from the phase in the approximation equation. Finally, an instantaneous frequency at time t is obtained from the instantaneous angular frequency. If the attenuation waveform is defined to be expressed in the above equation and the instantaneous frequency is then obtained, the instantaneous frequency may be obtained with higher accuracy even when an ultrasonic wave pulse signal having as small as one or two periods is used.

When using wavelet or Hilbert transform, the envelope line A(t) and the phase φ(t) of the attenuation waveform of a single-pulse ultrasonic wave signal having as small as one or two periods may be obtained readily and accurately.

A non-destructive testing system of the present invention comprises a pulse entering section configured to enter a single-pulse ultrasonic wave signal into an object to be tested; a receiving section configured to receive the single-pulse ultrasonic wave signal which has been entered into the object to be tested; a temporal change computing section configured to compute temporal change of an instantaneous frequency of an attenuation waveform of the received single-pulse ultrasonic wave signal; and a diagnosing section configured to diagnose a condition of the object to be tested, based on the temporal change of the instantaneous frequency computed by the temporal change computing section. The diagnosing section stores the temporal change of an instantaneous frequency, which have been measured in advance in respect of the object known to be in a normal condition, as at least one criterion for diagnosis. Then, the diagnosing section diagnoses the condition of the object to be tested by comparing the temporal change of the instantaneous frequency computed by the temporal change computing section with the at least one criterion for diagnosis. Since the non-destructive testing system of the present invention performs diagnosis by looking into the instantaneous frequency of the attenuation waveform of the single-pulse ultrasonic wave signal, the system is hardly affected by interference of reflected waves and is capable of detecting even a small amount of frequency change. In addition, the system of the present invention is higher in accuracy than conventional apparatuses of detecting harmonic and sub-harmonic components.

The pulse entering section generates a pulse signal having one or two periods and a frequency of 1 MHz to 10 MHz as a single-pulse ultrasonic wave signal. The temporal change computing section approximates an attenuation waveform u(t) of the received single-pulse ultrasonic wave signal using an approximation equation of u(t)=A(t)sin φ(t) where t stands for time, A(t) for an envelope line of the attenuation waveform and φ(t) for a phase at time t, obtains an instantaneous angular frequency at time t from the phase in the approximation equation, and obtains an instantaneous frequency at time t from the instantaneous angular frequency.

The pulse entering section and the receiving section may be disposed with respect to the object to be tested such that the receiving section receives the single-pulse ultrasonic wave signal which has transmitted the object to be tested or the receiving section receives the single-pulse ultrasonic wave signal which has been reflected inside the object to be tested.

BRIEF DESCRIPTION OF DRAWINGS

FIG. 5A illustrates an attenuation vibration waveform u(t), and FIG. 5B illustrates the result of wavelet transform of u(t).

MODES FOR CARRYING OUT INVENTION

Figure 1A:
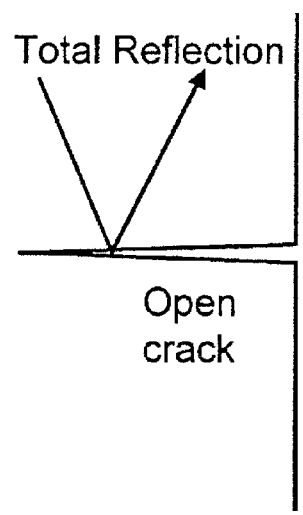
FIGS. 1A and 1B are illustrations used to explain ultrasonic testing method.
Figure 1B:
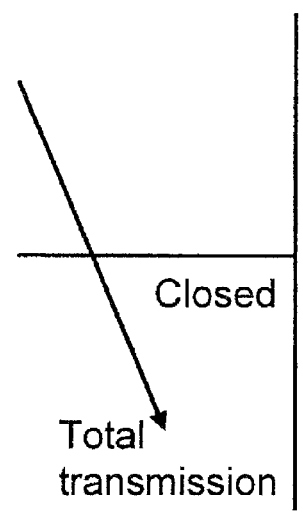
Figure 2:
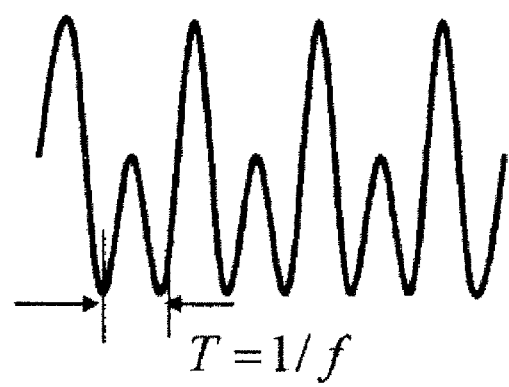
FIG. 2 illustrates example acoustic nonlinearity (½ (half) sub-harmonic wave).
Figure 3:
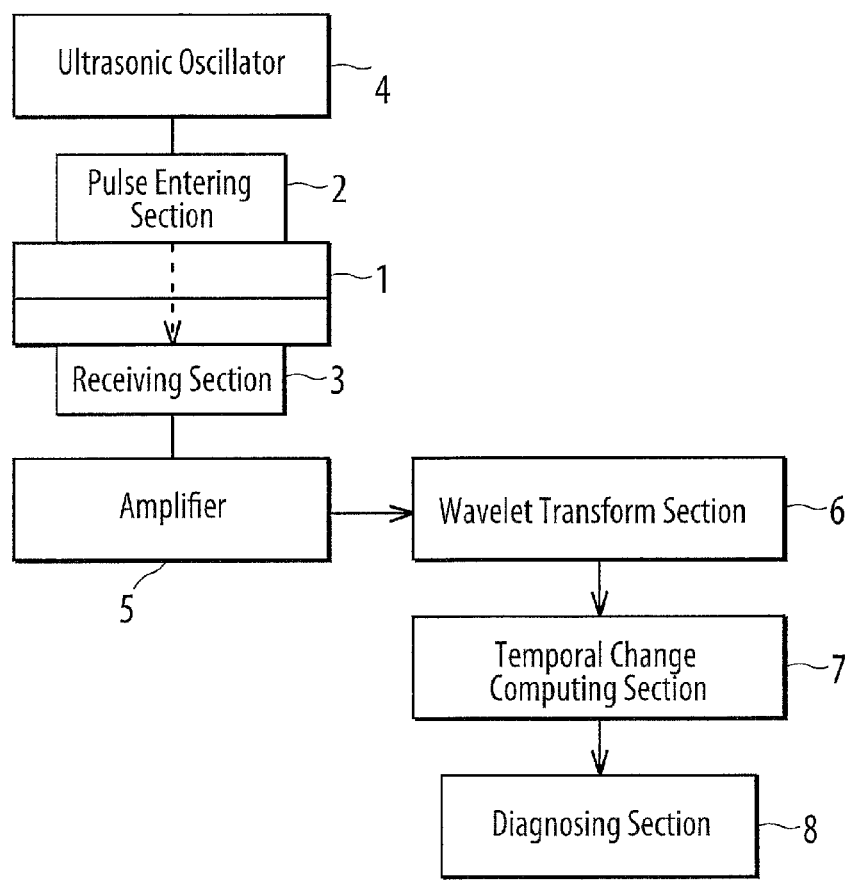
FIG. 3 illustrates an example configuration of a non-destructive testing system of the present invention.

Now, embodiments of a method and a system for non-destructive testing according to the present invention will be described in detail with reference to the accompanying drawings. FIG. 3 illustrates an example configuration of a non-destructive testing system of the present invention. Reference numeral 1 designates an object to be tested that is made of two rubber plates joined together. In this embodiment, a pulse entering section 2 configured to enter a single-pulse ultrasonic wave signal and a receiving section 3 configured to receive the incident single-pulse ultrasonic wave signal (or the single-pulse ultrasonic wave signal which has been entered into the object to be tested) are disposed to sandwich the object to be tested therebetween. An ultrasonic wave oscillator 4 transmits a pulse signal having a frequency of 1 MHz to 10 MHz and one or two periods to the pulse entering section 2. The pulse entering section 2 enters the single-pulse ultrasonic wave signal into the object to be tested. The receiving section 3 receives the single-pulse ultrasonic wave signal (transmitted wave) which has transmitted the inside of the object 1 to be tested. An attenuation waveform of the single-pulse ultrasonic wave signal received in the receiving section 3 is amplified by an amplifier 5 and then inputted to a wavelet transform section 6. The wavelet transform section 6 wavelet transforms the attenuation waveform to output an envelope line A(t) and a phase φ(t) of the attenuation waveform as discussed later. A temporal change computing section 7 uses the envelope line A(t) and the phase φ(t) of the attenuation waveform inputted from the wavelet transform section 6, and approximates the attenuation waveform using an approximation equation available for computing the attenuation waveform. Then, the temporal change computing section 7 obtains temporal change of an instantaneous frequency of the attenuation waveform of the received single-pulse ultrasonic wave signal. This computation process will be described later in detail. A diagnosing section 8 diagnoses a condition of the object to be tested, based on the temporal change of the instantaneous frequency computed by the temporal change computing section. The diagnosing section of this embodiment stores the temporal change of an instantaneous frequency, which have been measured in advance in respect of the object known to be in a normal condition, as at least one criterion for diagnosis. Then, the diagnosing section 8 diagnoses the condition of the object to be tested by comparing the temporal change of the instantaneous frequency computed by the temporal change computing section 7 with the at least one criterion for diagnosis.

The wavelet transform performed in the wavelet transform section 6 will be described below. The wavelet transform is defined as follows.

⟨Eq. 1⟩

$$(W_\psi f)(b, a) = \frac{1}{\sqrt{a}} \int_{-\infty}^{\infty} f(t) \overline{\psi\left(\frac{t-b}{a}\right)} dt \quad (1)$$

Here, ψ(t) stands for a local function called mother wavelet. In frequently used Gabor wavelet, the local function is expressed as follows.

⟨Eq. 2⟩

$$\psi(t) = \frac{1}{4\sqrt{\pi\alpha}} e^{-t^2/(4\alpha)} e^{i\omega_0 t} \quad (2)$$

Figure 4A:
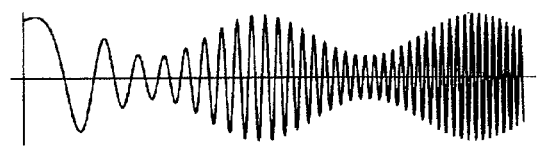
FIGS. 4A and 4B illustrate waveforms used to explain the wavelet transform.
Figure 4B:
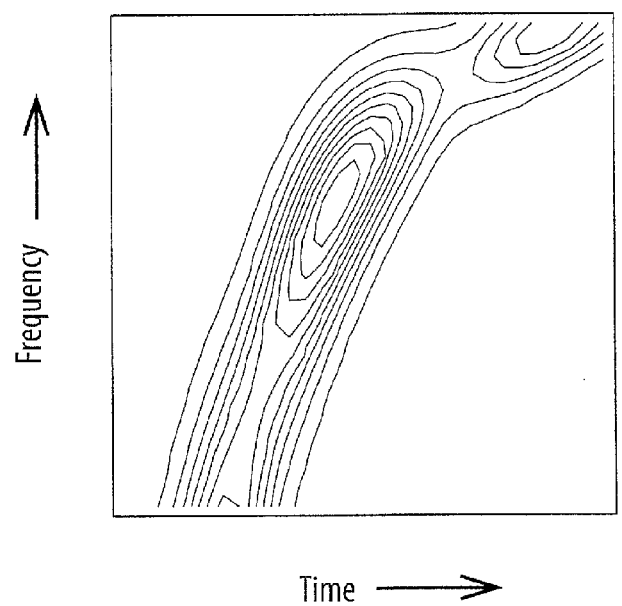

In the wavelet transform, the fundamental frequency component is represented by $\omega_0$. a is called scaling parameter which becomes smaller as the frequency component becomes higher. For example, when a is ½, the frequency component is $2\omega_0$. b is called translate parameter representing time information. The wavelet transform result $(W_\psi f)$ (b,a) shows the magnitude of a frequency component of $\omega_0/a$ at time b. The wavelet transform result $(W_\psi f)$ (b,a) is a complex number since ψ(t) is a complex number. Generally, the wavelet transform result is represented by [(real part)$^2$+(imaginary part)$^2$]$^{1/2}$ which is the magnitude of a complex number of $(W_\psi f)$ (b,a). For example, the wavelet transform result of a signal illustrated in FIG. 4A is shown in FIG. 4B. In FIG. 4B, the axis of abscissas indicates time which corresponds to b in Eq. (1) (Equation (1)) and the axis of ordinate indicates a frequency which corresponds to $\omega_0/a$ in Eq. (1). The contour lines of FIG. 4B represent the magnitude of frequency component at a particular time. It can be known from the figure that the frequency of a signal increases with the time.

Thus, the general wavelet transform is largely characterized in that it provides information on both time and frequency in terms of contour lines or color depth or thickness on a time-frequency domain.

Figure 5A:
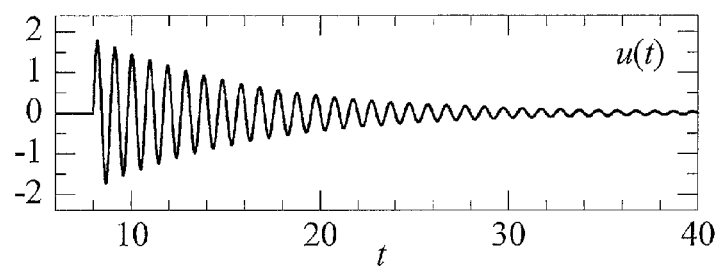
FIGS. 5A and 5B show wavelet transform examples. Specifically.

In the wavelet transform of this embodiment, the value of a is fixed to 1 (a=1) in Eq. (1). $\omega_0$ of Eq. (2) is the fundamental frequency in mother wavelet transform and is set to be coincident with the primary frequency of the ultrasonic wave pulse. For example, the wavelet transform is applied to a attenuation vibration waveform u(t) shown in FIG. 5A though it is not an ultrasonic waveform. Since a is fixed to 1 (a=1), the wavelet transform result will be a function having a translate parameter b alone. Defining that the result is represented by g(b), g(b) will be obtained by Eq. (3).

<Eq. 3>

$$g(b) = (W_\psi f)(b,1) = \int_{-\infty}^{\infty} u(t) \overline{\psi(t-b)} dt \quad (3)$$

Since the translate parameter b is equivalent to time t, the wavelet transform result is represented by g(t) by replacing an argument b with t. The result g(t) is a complex number and the attenuation waveform u(t) is approximated based on this result as follows. In the following Eq. (4), g'(t) is represented by g(t) with a bar indicated over g and g'(t) is a complex conjugate for g(t).

<Eq. 4>

$$u(t) \cong g(t) + \overline{g}(t) = 2\text{Re}[g(t)] \quad (4)$$

Figure 5B:
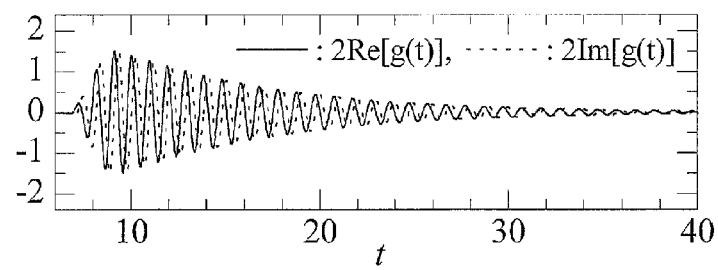

The result of the above equation is indicated with a solid line in FIG. 5B. It can be known from the figure that the waveform has been well approximated except for the rising of the attenuation waveform which is smoother than the original waveform u(t). For the imaginary part of g(t), 2Im[g(t)] is indicated with a dotted line in FIG. 5B. This corresponds to a phase shifted by ¼ period from the phase of 2Re[g(t)]. The attenuation waveform u(t) may be approximated using these relationships as follows:

⟨Eq. 5⟩

$$u(t) \cong A(t) \sin\phi(t) \quad (5)$$
$$A(t) = 2\sqrt{\text{Re}[g(t)]^2 + \text{Im}[g(t)]^2}$$
$$\phi(t) = \tan^{-1} \frac{\text{Im}[g(t)]}{\text{Re}[g(t)]}$$

In the above equation, A(t) stands for an amplitude at time t and represents an envelope line of the attenuation waveform and φ(t) stands for a phase at time t. Time differential of φ(t) corresponds to an instantaneous angular frequency ω(t) of the attenuation waveform at time t. The instantaneous angular frequency ω(t) is expressed as follows:

⟨Eq. 6⟩

$$\omega(t) = \frac{d\phi(t)}{dt} \quad (6)$$

The instantaneous frequency f(t) at time t is expressed as follows:

<Eq. 7>

$$f(t) = \omega(t)/2\pi \quad (7)$$

The differential part of Eq. (6) is numerically calculated.

The temporal change computing section 7 approximates the attenuation waveform u(t) of the received single-pulse ultrasonic wave signal using an approximation equation of u(t)=A(t)sin φ(t) which is obtained from Eq. (5) of wavelet transform represented by an envelope line A(t) of the attenuation waveform and a phase φ(t) at time t. Then, the instantaneous angular frequency ω(t) at time t is obtained from the phase ϕ(t) in the approximation equation. Finally, the instantaneous frequency f(t) at time t is obtained from the instantaneous angular frequency ω(t).

Figure 6A:
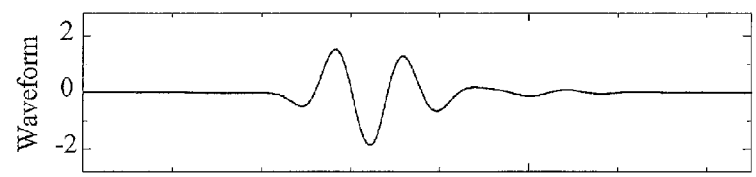
FIG. 6A illustrates an ultrasonic wave pulse which has transmitted a rubber plate.
Figure 6B:
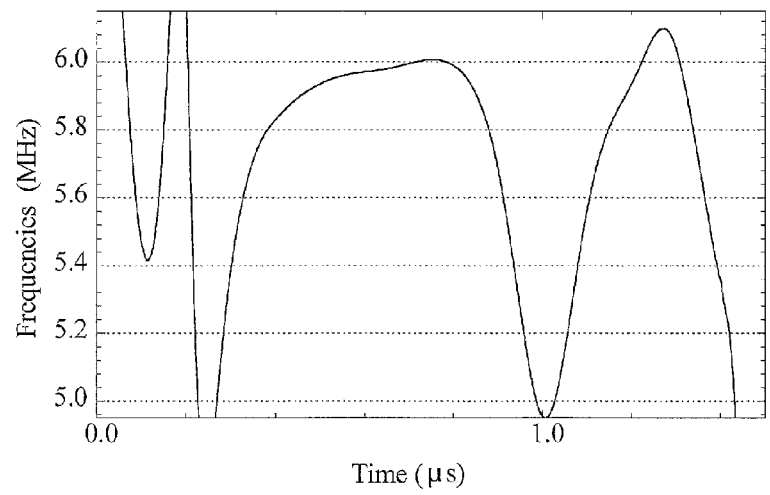
FIG. 6B illustrates temporal change of the frequency.

Next, a specific experimental example will be described. First, a pressure was applied to a rubber plate having a thickness of about 2 mm. The pulse entering section 2 was disposed on one side of the rubber plate which was an object to be tested, and entered a single-pulse ultrasonic wave signal into the object to be tested. The receiving section 3 was disposed on the other side of the rubber plate and received the signal. FIG. 6A illustrates an ultrasonic wave pulse received by the receiving section 3. FIG. 6B illustrates temporal change or temporal transition of the instantaneous frequency of the ultrasonic wave pulse computed by the temporal change computing section 7. The diagnosing section 8 stored the temporal change or transition of the instantaneous frequency shown in FIG. 6B as a criterion for diagnosis. In an example of FIG. 6B, it can be observed that the frequency of the attenuation waveform of a single-pulse ultrasonic wave signal slightly increased around 6 MHz as the time elapsed. In FIG. 6B, the waveform shown in the middle is a reference waveform used as a criterion for diagnosis, and waveforms appearing on either side are noise waveforms.

Figure 7A:
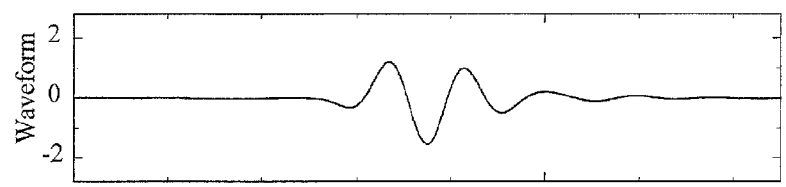
FIG. 7A illustrates an ultrasonic wave pulse which has transmitted two rubber plates piled with pressure.
Figure 7B:
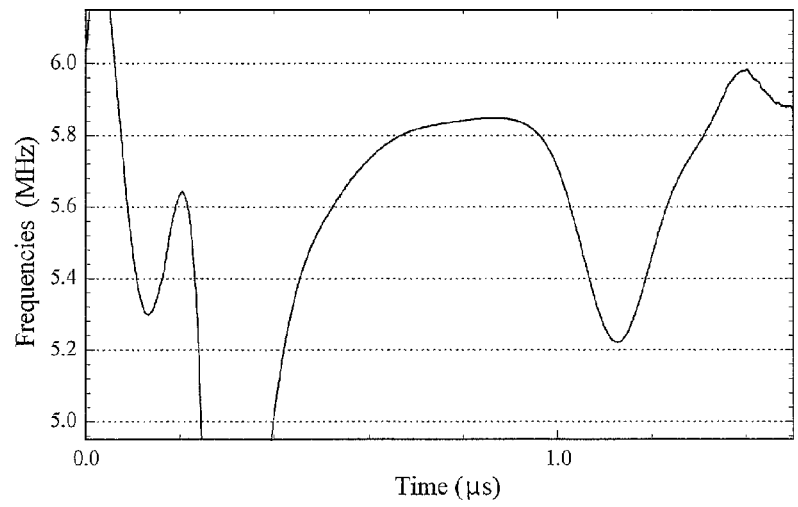
FIG. 7B illustrates temporal change of the frequency.

Second, the same pressure as the first example having a thickness of 2 mm was applied to two rubber plates each having a thickness of 1 mm and piled or stacked together. An imperceptible gap existed between the two rubber plates. As with the first example, the pulse entering section 2 disposed on one side of the rubber plates entered a single-pulse ultrasonic wave signal into the rubber plates and the receiving section 3 disposed on the other side of the rubber plates received the transmitted signal. FIG. 7A illustrates an example attenuation waveform of the ultrasonic wave pulse signal thus obtained. FIG. 7B illustrates the temporal change or transition of the instantaneous frequency of the attenuation waveform. In FIG. 7B as with FIG. 6B, the waveform shown in the middle is a reference waveform used as a criterion for diagnosis, and waveforms appearing on either side are noise waveforms.

In comparing FIG. 7A with and FIG. 6A, the waveforms of the ultrasonic wave pulse signal received by the receiving section 3 are almost the same. However, an apparent decrease in temporal change of the instantaneous frequency can be observed around 5.8 MHz in FIG. 7A. It can be inferred from this that an imperceptible gap existed between the rubber plates in view of the apparent decrease in temporal change of the instantaneous frequency. The diagnosing section 8 performed diagnosis by utilizing comparison between the patterns of temporal change of instantaneous frequency.

Figure 8:
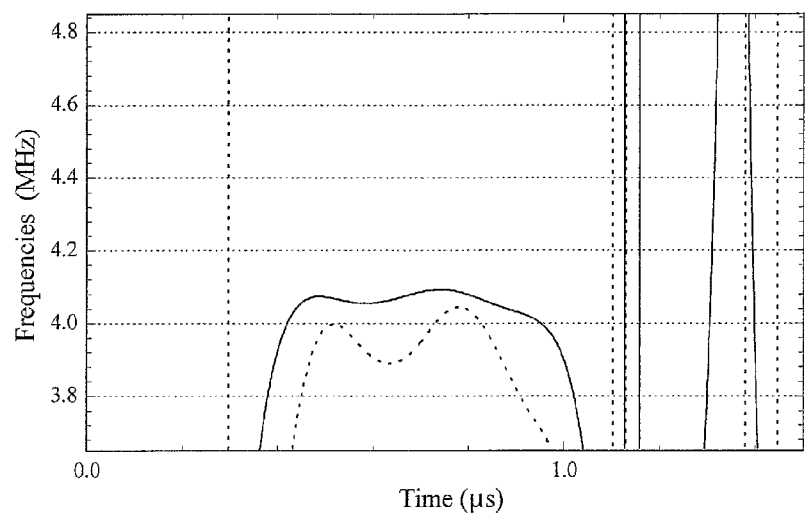
FIG. 8 illustrates differences in frequency change due to differences in pressing force applied between the two rubber plates wherein solid lines indicate high pressing force and dotted lines indicate low pressing force.

As described so far, how the instantaneous frequency of the single-pulse ultrasonic wave signal temporally changes or changes with the time depends upon the contact condition of interface inside an object. As a result, the contact condition of interface inside an object can be inferred based on the temporal change of the instantaneous frequency. A similar experiment to the experiment as described above was performed. In FIG. 8, the temporal change of the instantaneous frequency when a high pressure was applied to the rubber plates is indicated with solid lines, and the temporal change of the instantaneous frequency when a low pressure was applied to the rubber plates is indicated with dotted lines. As known from FIG. 8, the pattern of temporal change of the instantaneous frequency varies like swelling as indicated with a dotted line in case of low pressure. This is quite different from the pattern of temporal change of the instantaneous frequency as indicted with a solid line in case of high pressure. It is also known from the figure that an average frequency decreased. It follows from this that it is possible to infer a difference in compressing force applied to the rubber plates, namely a difference in contact condition between the rubber plates. In FIG. 8 as with FIGS. 6B and 7B, the waveform shown in the middle is a reference waveform used as a criterion for diagnosis, and waveforms appearing on either side are noise waveforms.

Figure 9:
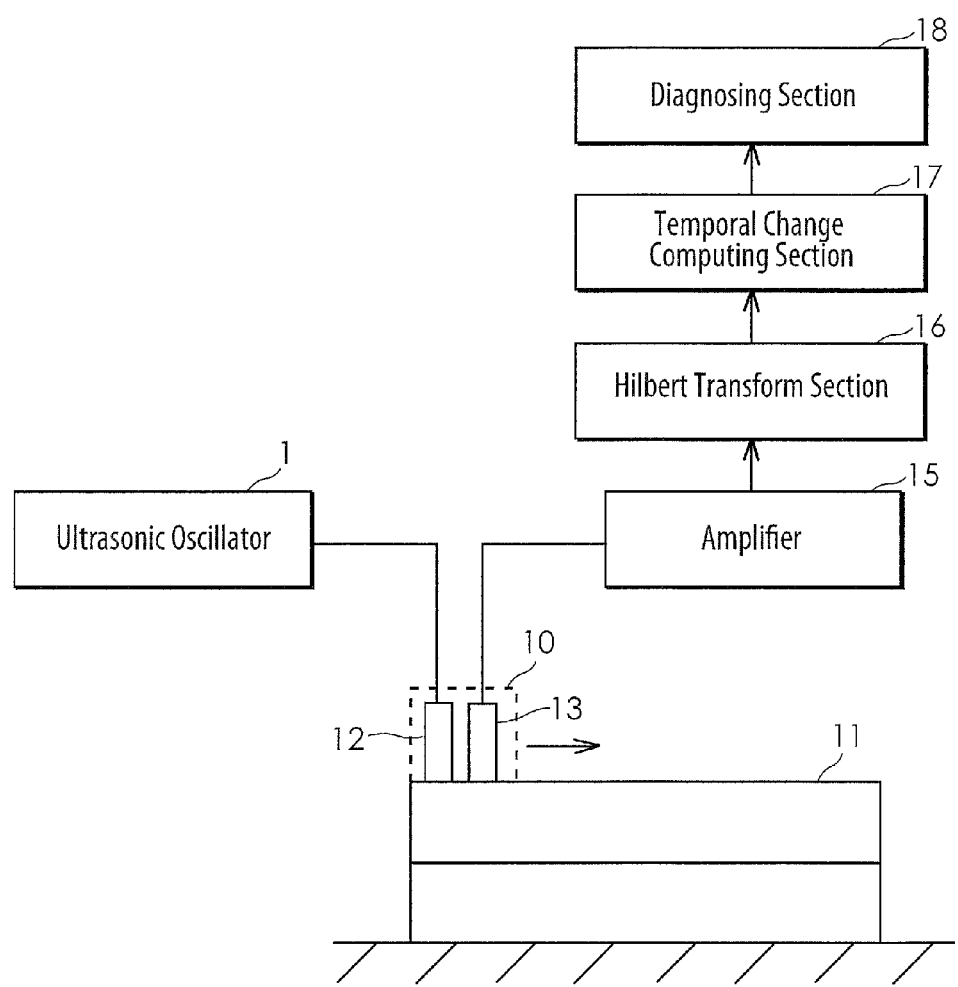
FIG. 9 illustrates an example configuration of a non-destructive testing system used for diagnosis based on reflected waves.

This embodiment of the present invention as described so far is directed to transmitted waves. The present invention is also applicable to reflected waves. The diagnosis may be possible based on the pulse signal which enters an object to be tested and is reflected at a reflection layer such as a gap layer and a material change layer inside the object to be tested. FIG. 9 illustrates an example configuration of a non-destructive testing system used for diagnosis based on reflected waves. Parts of the example of FIG. 9 that are similar to those of the example of FIG. 3 (a non-destructive testing system used for diagnosis based on transmitted waves) are designated with reference numerals obtained by adding 10 to the reference numerals allocated to their counterparts of FIG. 3. This embodiment uses a sensor unit 10 including a pulse entering section 12 and a receiving section 13 such that the pulse entering section 12 enters a single-pulse ultrasonic wave signal into an object 11 to be tested and the receiving section 13 receives a plurality of reflected waves of the single-pulse ultrasonic wave signal that have been reflected inside the object. The receiving section 13 receives the reflected waves as the sensor unit 10 is moved along the surface of the object to be tested. This embodiment employs a Hilbert transform section 16 in place of the wavelet transform section 6 of FIG. 3 in order to obtain an envelope line A(t) and a phase ϕ(t) of the attenuation waveform of the reflected wave. A function h(t) obtained from the Hilbert transform of the reflected wave is defined as follows:

⟨Eq. 8⟩

$$h(t) = \frac{1}{\pi} \int_{-\infty}^{\infty} \frac{u(S)}{t-s} ds \qquad (8)$$

In the above equation, u(s) stands for an attenuation waveform of the single-pulse ultrasonic wave signal and s for an integral parameter. The Hilbert transform result h(t) corresponds to the phase shifted by π/4 period from u(t). The phase ϕ(t) at time t is obtained as follows:

⟨Eq. 9⟩

$$\phi(t) = \tan^{-1} \frac{h(t)}{u(t)} \qquad (9)$$

The instantaneous frequency f(t) at time t is obtained as follows:

⟨Eq. 10⟩

$$f(t) = \frac{1}{2\pi} \frac{d\phi(t)}{dt} \qquad (10)$$

A temporal change computing section 17 computes the instantaneous frequency based on the above equation and obtains temporal change of the instantaneous frequency in the same manner as the temporal change computing section 7 does.

Figure 10:
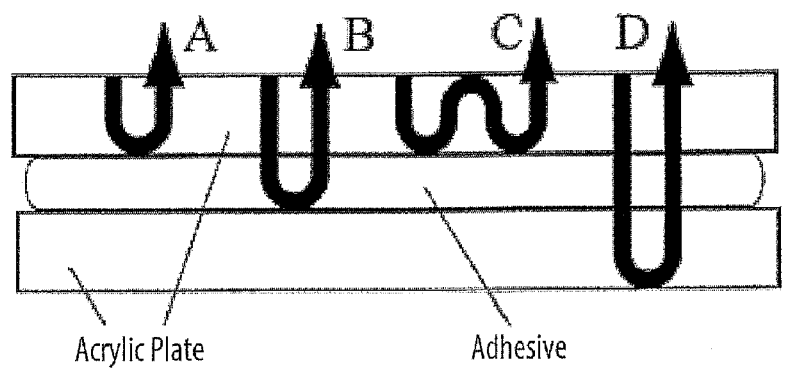
FIG. 10 illustrates a specimen structure and estimated paths of reflected waves.

Also in this embodiment, an experiment was performed in order to confirm that an effect could be obtained. The experiment was intended to confirm feasibility for the evaluation of adhesion strength of an adhesive as diagnosis of an inner condition of an object under test. A specimen to be tested was prepared as an object to be tested. The specimen was simply made of two acrylic plates adhered together with an epoxy-based adhesive as shown in FIG. 10. The two plates were adhered to each other under the following three different conditions. The adhesives used in the experiment generally required 10 minutes or less after the application in order to obtain specified adhesion strength. Therefore, the longer time is required from the application of the adhesive till the completion of adhesion, the less adhesion strength will be.

[Condition 1] 20 minutes required from the application of the adhesive till the completion of adhesion (Low adhesion strength)

[Condition 2] 10 minutes required from the application of the adhesive till the completion of adhesion (Medium adhesion strength)

[Condition 3] Adhesion quickly completed from the application of the adhesive (High adhesion strength)

Figure 11:
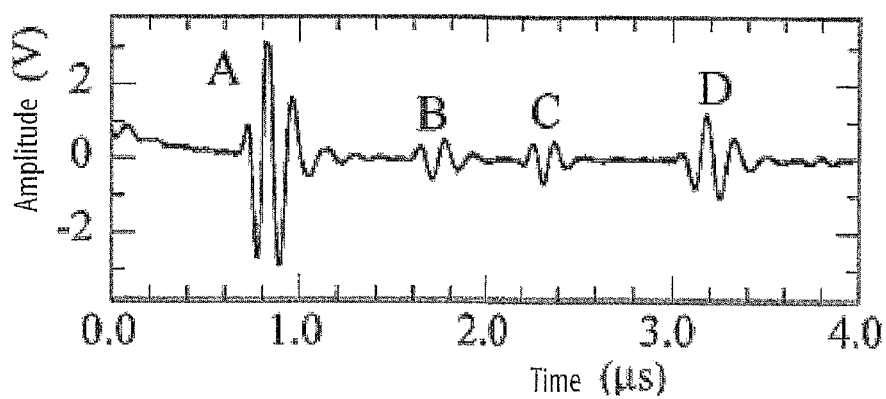
FIG. 11 illustrates the waveforms of four reflected pulses A, B, C, and D as received when single-pulse ultrasonic wave signals are used.

The non-destructive testing system shown in FIG. 9 was used. The single-pulse ultrasonic wave signal was entered into the specimen from one side thereof, and the ultrasonic wave pulse signal, which had been reflected inside the specimen, was measured as shown in FIG. 10. Four reflected waves A, B, C, and D respectively having waveforms shown in FIG. 11 were received when entering a single-pulse ultrasonic wave signal into the specimen under condition 1. It may be inferred that the waves were reflected along paths A, B, C, and D shown in FIG. 10. Although the illustrations showing the reflected pulses under conditions 2 and 3 are omitted, any significant difference in velocities and amplitudes of the reflected pulses A to D under the different conditions could not be confirmed from the measurement data. Further, it was impossible to clearly find out any difference in frequency components under the different conditions even by performing the segmental analysis of the frequencies of the reflected pulses A to D, and obtaining the respective frequency spectra. In short, it was confirmed that conditions 1 to 3 could not be distinguished based on the changes in velocities, amplitudes and frequency components.

Figure 12:
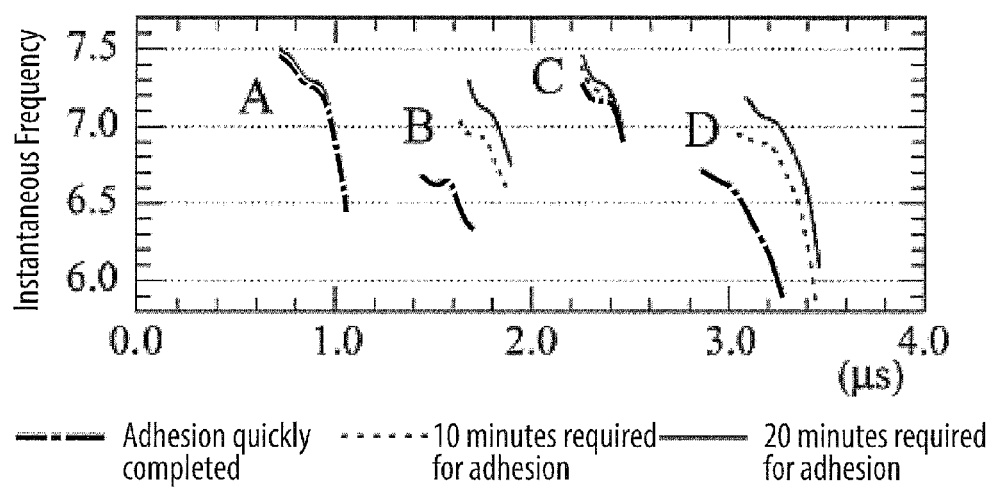
FIG. 12 illustrates the temporal changes of the instantaneous frequencies of the reflected pulses A, B, and C under three different conditions.

FIG. 12 illustrates the temporal changes of the instantaneous frequencies of the reflected pulses A to D under three conditions 1 to 3. In FIG. 12, the experiment result under condition 1 (20 minutes required for adhesion) is indicated with black lines, the one under condition 2 (10 minutes required for adhesion) is indicated with dotted lines, and the one under condition 3 (quickly completed adhesion) is indicated with gray lines. The temporal changes of instantaneous frequencies of reflected pulses A and C, which had transmitted only the acrylic portion, hardly differed under conditions 1 to 3. However, the temporal changes of instantaneous frequencies of reflected pulses B and D, which had transmitted the adhesive portion, significantly differed under conditions 1 to 3. The more quickly adhesion was completed after the application of the adhesive, namely, the higher the adhesion strength was, the less the temporal change of instantaneous frequency of the reflected pulse was. Therefore, it may be possible to evaluate adhesion strength based on the temporal change of instantaneous frequency of the reflected pulse which transmitted the adhesive portion. Such clear or distinct difference cannot be found out in view of an ordinary frequency spectrum. It has been confirmed that a method of the present embodiment focusing on the temporal change of instantaneous frequency is effective.

The embodiments described so far employ the wavelet and Hilbert transforms to obtain the instantaneous frequency of the attenuation waveform of a single-pulse ultrasonic wave signal. However, the present invention does not stick to the wavelet and Hilbert transforms. Other publicly known methods may be employed, provided that the temporal change of an instantaneous frequency of an attenuation waveform of an ultrasonic wave pulse signal can be obtained by such publicly known methods.

INDUSTRIAL APPLICABILITY

According to the present invention, a general ultrasonic testing apparatus can be used since a single-pulse ultrasonic wave signal is used. The single-pulse ultrasonic wave signal refers to a pulse signal having as small as one or two periods and the testing is hardly affected by interference of reflected waves. Therefore, according to the present invention, it is possible to detect even slight temporal change of instantaneous frequency of the attenuation waveform and to perform more accurate diagnosis than methods focusing on harmonic and sub-harmonic components.

DESCRIPTION OF REFERENCE NUMERALS 1, 11 Object to be tested
2, 12 Pulse entering section
3, 13 Receiving section
4, 14 Ultrasonic oscillator
5, 15 Amplifier
6 Wavelet transform section
16 Hilbert transform section
7, 17 Temporal change computing section
8, 18 Diagnosing section

The invention claimed is:

1. A non-destructive testing method comprising the steps of:
   entering a single-pulse ultrasonic wave signal from a pulse entering section into an object to be tested, the single-pulse ultrasonic wave signal having one or two periods and a frequency of 1 MHz to 10 MHz;
   receiving the single-pulse ultrasonic wave signal, which has been entered into the object to be tested, in a receiving section; and
   approximating an attenuation waveform u(t) of the received single-pulse ultrasonic wave signal using an approximation equation of $u(t)=A(t)\sin\phi(t)$ where t stands for time, $A(t)$ for an envelope line of the attenuation waveform and $\phi(t)$ for a phase at time t;
   obtaining an instantaneous angular frequency at time t from the phase in the approximation equation;
   obtaining an instantaneous frequency at time t from the instantaneous angular frequency; and
   diagnosing a condition of the object to be tested, based on temporal change of the instantaneous frequency.

2. The non-destructive testing method according to claim 1, wherein the received single-pulse ultrasonic wave signal is a transmitted wave which has transmitted the object to be tested.

3. The non-destructive testing method according to claim 1, wherein the received single-pulse ultrasonic wave signal is a reflected wave which has been reflected inside the object to be tested.

4. The non-destructive testing method according to claim 1, wherein the envelope line A(t) of the attenuation waveform and the phase φ(t) are obtained using wavelet transform.

5. The non-destructive testing method according to claim 1, wherein the condition of the object to be tested is diagnosed by comparing a pattern shape of temporal change of the instantaneous frequency in respect of the object to be tested with a pattern shape of temporal change of an instantaneous frequency, which is used as a reference and has been obtained in advance by measuring the temporal change of the instantaneous frequency in respect of the object known to be in a normal condition.

6. A non-destructive testing method comprising the steps of:

entering a single-pulse ultrasonic wave signal into an object to be tested;

receiving the single-pulse ultrasonic wave signal which has been entered into the object to be tested;

obtaining temporal change of an instantaneous frequency of an attenuations waveform of the received single-pulse ultrasonic wave signal; and diagnosing a condition of the object to be tested, based on the temporal change of the instantaneous frequency.

7. The non-destructive testing method according to claim 6, wherein the single-pulse ultrasonic wave signal has one or two periods and a frequency of 1 MHz to 10 MHz.

8. The non-destructive testing method according to claim 6, wherein:

the attenuation waveform u(t) of the received single-pulse ultrasonic wave signal is approximated using an approximation equation of u(t)=A(t)sin φ(t) where t stands for time, A(t) for an envelope line of the attenuation waveform and φ(t) for a phase at time t;

the instantaneous angular frequency at time t is obtained from the phase in the approximation equation; and the instantaneous frequency at time t is obtained from the instantaneous angular frequency.

9. The non-destructive testing method according to claim 6, wherein the received single-pulse ultrasonic wave signal is a transmitted wave which has transmitted the object to be tested.

10. The non-destructive testing method according to claim 6, wherein the received single-pulse ultrasonic wave signal is a reflected wave which has been reflected inside the object to be tested.

11. The non-destructive testing method according to claim 6, wherein the envelope line A(t) of the attenuation waveform and the phase φ(t) are obtained using wavelet transform.

12. The non-destructive testing method according to claim 6, wherein the condition of the object to be tested is diagnosed by comparing a pattern shape of temporal change of the instantaneous frequency in respect of the object to be tested with a pattern shape of temporal change of an instantaneous frequency, which is used as a reference and has been obtained in advance by measuring the temporal change of the instantaneous frequency in respect of the object known to be in a normal condition.

13. A non-destructive testing system comprising:

a pulse entering section configured to enter a single-pulse ultrasonic wave signal into an object to be tested;

a receiving section configured to receive the single-pulse ultrasonic wave signal which has been entered into the object to be tested;

a temporal change computing section configured to compute temporal change of an instantaneous frequency of an attenuation waveform of the received single-pulse ultrasonic wave signal; and a diagnosing section configured to diagnose a condition of the object to be tested, based on the temporal change of the instantaneous frequency computed by the temporal change computing section.

14. The non-destructive testing system according to claim 13, wherein the diagnosing section stores the temporal change of an instantaneous frequency, which have been measured in advance in respect of the object known to be in a normal condition, as at least one criterion for diagnosis; and the condition of the object to be tested is diagnosed by comparing the temporal change of the instantaneous frequency computed by the temporal change computing section with the at least one criterion for diagnosis.

15. The non-destructive testing system according to claim 14, wherein:

the pulse entering section generates a pulse signal having one or two periods and a frequency of 1 MHz to 10 MHz as a single-pulse ultrasonic wave signal; and the temporal change computing section approximates an attenuation waveform u(t) of the received single-pulse ultrasonic wave signal using an approximation equation of u(t)=A(t)sin φ(t) where t stands for time, A(t) for an envelope line of the attenuation waveform and φ(t) for a phase at time t, obtains the instantaneous angular frequency at time t from the phase in the approximation equation, and obtains the instantaneous frequency at time t from the instantaneous angular frequency.

16. The non-destructive testing system according to claim 13, wherein the pulse entering section and the receiving section are disposed with respect to the object to be tested such that the receiving section receives the single-pulse ultrasonic wave signal which has been reflected inside the object to be tested.

17. The non-destructive testing system according to claim 13, wherein the pulse entering section and the receiving section are disposed with respect to the object to be tested such that the receiving section receives the single-pulse ultrasonic wave signal which has transmitted the object to be tested.

* * * * *